(12) United States Patent
Smith et al.

(10) Patent No.: US 7,126,104 B2
(45) Date of Patent: Oct. 24, 2006

(54) SYSTEM AND METHOD FOR IDENTIFYING, REPORTING, AND EVALUATING PRESENCE OF SUBSTANCE

(75) Inventors: Maurice Smith, Kansas City, MO (US); Michael Lusby, Kansas City, MO (US); Arthur Van Hook, Lake Lotawana, MO (US); Charles J. Cook, Raytown, MO (US); Edward G. Wenski, Lenexa, KS (US); David Solyom, Overland Park, KS (US)

(73) Assignee: Honeywell Federal Manufacturing & Technologies, LLC, Kansas City, MO (US)

( * ) Notice: Subject to any disclaimer, the term of this patent is extended or adjusted under 35 U.S.C. 154(b) by 511 days.

(21) Appl. No.: 10/672,210

(22) Filed: Sep. 26, 2003

(65) Prior Publication Data

US 2005/0171701 A1    Aug. 4, 2005

Related U.S. Application Data

(60) Provisional application No. 60/414,507, filed on Sep. 26, 2002.

(51) Int. Cl.
*H01J 40/14*      (2006.01)
(52) U.S. Cl. .................................... 250/221; 250/559.4
(58) Field of Classification Search ................ 250/221, 250/559.4
See application file for complete search history.

(56) References Cited

U.S. PATENT DOCUMENTS

| | | | |
|---|---|---|---|
| 4,861,727 A | 8/1989 | Hauenstein et al. | |
| H1344 H | 8/1994 | Baldauf et al. | |
| 5,444,444 A | 8/1995 | Ross | |
| 5,470,233 A | 11/1995 | Fruchterman et al. | |
| 5,528,248 A | 6/1996 | Steiner et al. | |
| 5,648,914 A | 7/1997 | Bauer et al. | |
| 5,650,800 A | 7/1997 | Benson | |
| 5,838,237 A | 11/1998 | Revell et al. | |
| 5,938,721 A | 8/1999 | Dussell et al. | |
| 5,972,638 A | 10/1999 | Burlage et al. | |
| 6,023,223 A | 2/2000 | Baxter, Jr. | |
| 6,052,187 A | 4/2000 | Krishnan et al. | |
| 6,075,891 A | 6/2000 | Burman | |
| 6,083,248 A | 7/2000 | Thompson | |
| 6,169,476 B1 | 1/2001 | Flanagan | |
| 6,317,080 B1 | 11/2001 | Baxter, Jr. | |
| 6,327,535 B1 | 12/2001 | Evans et al. | |

(Continued)

OTHER PUBLICATIONS

"Oak Ridge claims sensitivity record for Si MEMS sensor"; Jun. 23, 2003 article in Electronic Engineering Times; Author R. Colin Johnson, p. 49.

*Primary Examiner*—Que T. Le
(74) *Attorney, Agent, or Firm*—Hovey Williams LLP

(57) ABSTRACT

A system and method for identifying, reporting, and evaluating a presence of a solid, liquid, gas, or other substance of interest, particularly a dangerous, hazardous, or otherwise threatening chemical, biological, or radioactive substance. The system comprises one or more substantially automated, location self-aware remote sensing units; a control unit; and one or more data processing and storage servers. Data is collected by the remote sensing units and transmitted to the control unit; the control unit generates and uploads a report incorporating the data to the servers; and thereafter the report is available for review by a hierarchy of responsive and evaluative authorities via a wide area network. The evaluative authorities include a group of relevant experts who may be widely or even globally distributed.

7 Claims, 6 Drawing Sheets

U.S. PATENT DOCUMENTS

| | | |
|---|---|---|
| 6,356,625 B1 | 3/2002 | Castellani et al. |
| 6,446,004 B1 | 9/2002 | Cao et al. |
| 6,490,530 B1 | 12/2002 | Wyatt |
| 6,498,041 B1 | 12/2002 | Tabacco et al. |
| 6,588,701 B1 | 7/2003 | Yavnai |
| 6,608,559 B1 | 8/2003 | Lemelson et al. |
| 6,628,941 B1 | 9/2003 | Knoblach et al. |
| 6,670,887 B1 * | 12/2003 | Dungan ............... 340/632 |

* cited by examiner

SYSTEM AND METHOD FOR IDENTIFYING, REPORTING, AND EVALUATING PRESENCE OF SUBSTANCE

RELATED APPLICATIONS

The present non-provisional patent application claims, with regard to all common subject matter, priority benefit of a copending provisional patent application titled PORTABLE IMAGE RECOGNITION & ANALYSIS TRANSDUCERS EQUIPMENT (PIRATE); Ser. No. 60/414,507; filed: Sep. 26, 2002. The identified provisional patent application is hereby incorporated by reference into the present non-provisional patent application.

FEDERALLY SPONSORED RESEARCH OR DEVELOPMENT PROGRAM

The present invention was developed with support from the U.S. government under Contract No. DE-AC04-01AL66850 with the U.S. Department of Energy. Accordingly, the U.S. government has certain rights in the present invention.

BACKGROUND OF THE INVENTION

1. Field of the Invention

The present invention relates broadly to systems and methods for detecting, identifying, reporting, and evaluating presences of substances. More particularly, the present invention concerns a system and method for identifying, reporting, and evaluating a presence of a solid, liquid, gas, or other substance of interest, particularly a dangerous, hazardous, or otherwise threatening chemical, biological, or radioactive substance. The system comprises one or more substantially automated, location self-aware remote sensing units; a control unit; and one or more data processing and storage servers. Data is collected by the remote sensing units and transmitted to the control unit; the control unit generates and uploads a report incorporating the data to the servers; and thereafter the report is available for review by a hierarchy of responsive and evaluative authorities via a wide area network. The evaluative authorities include a group of relevant experts who may be widely or even globally distributed.

2. Description of the Prior Art

It is often desirable to monitor for, identify, report, and evaluate a presence of a solid, liquid, gaseous, or other substance of interest. It will be appreciated, for example, that it has become highly desirable or even necessary, particularly in light of recent terrorist activities, to monitor for, identify, report, and evaluate any presence of threatening chemical, biological, or radioactive substances. Many less sinister substances, however, are also often the subject of monitoring, including, for example, pollutants; illegal or otherwise regulated substances; substances of interest to science; and substances of interest to agriculture or industry.

In the case of threatening substances, for example, detection devices are well-known in the prior art, ranging from the extremely simple to the exceedingly complex. Simple detection devices are typically narrowly capable of detecting and identifying a single substance or group of closely related substances. These extremely limited devices typically combine detection and identification into a single function by using a very specific test that can only detect the presence or non-presence of the specific substance and none other. An expensive and unwieldy collection of these simple devices would be needed in order to monitor or test for the wide variety of substances that might pose threats to health and safety. Unfortunately, providing such a collection of devices on a deployable mobile platform suitable for field testing substances whenever and wherever they may be encountered would be difficult and impractical at best. Furthermore, even if such a large and expensive mobile collection were created, it most likely could not be introduced into a suspect area in a timely manner and without undue risk to its operators. Additionally, unless multiple instances of each device are included in the collection, there is no redundancy to ameliorate failure, such as malfunction or mistake, by any particular device.

Furthermore, because these simple devices are often designed for stand-alone operation, integrating their systems, particularly their disparate operating and reporting systems, would be an exceedingly difficult and costly task. Relatedly, even if such integration were achieved, replacing an older version of a device with a newer version might well require substantial additional integration work, thereby providing a powerful disincentive for upgrading to newer and better devices whenever possible. Additionally, being substantially disparate and designed without concern for integration, these simple devices are unable to communicate or cooperate with one another in performing their respective functions. Thus, a particular detection device of the collection may be engaged in substantial and time-consuming testing while all other devices sit inefficiently idle.

Prior art complex detection devices are generally more broadly capable than the above-described simple devices, but they also suffer from a number of disadvantages. More specifically, increased capability is typically associated with an increase in operational complexity, requiring substantial investments in initial and continued training so that the complex devices can be used properly and effectively. Furthermore, the devices require substantial operational control by and interaction with a human operator either in physical contact or close proximity with the detection device. It will be appreciated that this necessarily exposes the operator to the substance being tested, thereby requiring the operator to wear extremely cumbersome protective gear. This gear, in turn, makes operating any small buttons, dials, or other input or control mechanisms on the device extremely difficult.

Relatedly, a lack of any substantial automation of the device means that testing can only be performed once the necessary human operator arrives on the scene, precluding both continuous monitoring and the fastest possible identification of the substance. Thus, only once there is reason to suspect that the substance is present (possibly as a result of animal or human deaths) might an order be given to deploy the human operator and the detection device. Thereafter, the human operator must travel to the scene and prepare for and perform the appropriate testing while wearing cumbersome protective gear and otherwise avoiding exposing himself or herself to the potentially hazardous substance. Furthermore, though it may be established that the substance is not one of the particular substances being tested for, actual identification of the substance may not be accomplished. During this very inefficient and time-consuming procedure, a large number of additional people may be exposed to the threatening substance depending on such factors as wind, rain, other weather conditions; insect, animal, or human movements; or other vectors.

Once a positive identification has been made or, at least, the presence of certain substances has been ruled out, the results observed by the operator of the device is typically reported to a remote team member using short range two-way radios. The remote team member must then transcribe or enter these reports before they can be relayed to a higher authority. This inefficient process further delays initiation of any response to the threat, and may introduce communication and transcription errors.

Additionally, prior art devices typically do not allow for quick and convenient removal and replacement of malfunctioning or obsolete components. When a malfunction occurs, the device must be taken out of service until appropriate maintenance can be performed by a qualified technician. When improved sensors or other components become available, the entire device must be replaced at substantial cost in order to obtain the benefit of improved performance. Relatedly, the devices are typically not customizable with regard to performance, capability, or cost.

Additionally, prior art devices typically have no capability to identify appropriate local, state, or regional contacts for reporting detection of a threatening substance. Typically, individual detection devices or collections of such devices are deployed by state or federal agencies and report only to a particular high-level authority rather than a local authority (e.g., city or county). Thus, once information has been gathered, it is disseminated, if at all, using a top-down model, which can result in substantial delay between initial notification of the state or federal authorities and notification of the local authorities who are charged with responding to the threatening situation, and can result in substantial confusion if the information is misinterpreted or miscommunicated as it is repeated up and down this chain. Furthermore, local authorities may have particular protocols or policies in place for such reporting that are not available or not followed when notifying them of the hazard or threat, thereby further undermining any possibility of a timely response to the situation.

Due to the above-identified and other problems and disadvantages in the art, a need exists for an improved system and method of identifying, reporting, and evaluating presences of substances, particularly threatening substances.

SUMMARY OF THE INVENTION

The present invention overcomes the above-described and other problems and disadvantages encountered in the prior art by providing a system and method for identifying, reporting, and evaluating a presence of one or more solids, liquids, gases, or other substances of interest, particularly dangerous, hazardous, or otherwise threatening chemical, biological, or radioactive substance.

In a preferred embodiment, the system broadly comprises one or more remote sensing units, hereinafter referred to as "IRAM units" ("Image Recording and Analysis Methods" units); one or more communications and control units, hereinafter referred to as "OATS units" ("Open Architecture Transmission and Supervision" units); a wide area telecommunications network; and one or more remote data processing and storage servers. Once the substance of interest is detected, the OATS unit generates and uploads a report detailing its presence and other relevant information to the servers, whereafter the report is available for review by a hierarchy of response and evaluation authorities via the wide area network.

Each IRAM unit is adapted and operable to substantially automatically and independently gather sensor and other data from within an area of interest and communicate this data to the OATS unit. Each IRAM unit preferably includes a position-determining mechanism; a sample collector mechanism; a sample examination cassette; a data collection mechanism for collecting identifying and other relevant information concerning the substance; temperature, wind speed/direction, and rain sensors; a transceiver; a power supply; and a local warning device. The IRAM unit uses an open architecture or interface that allows for easily and conveniently removing and replacing the components (so called "plug-and-play") without having to restart or reboot the IRAM unit (so-called "hot-swapping"), thereby facilitating easy, convenient, and cost-effective removal and replacement of unneeded, malfunctioning, or obsolete components.

The position-determining mechanism automatically and continually determines a particular geographic position or location of the IRAM unit. The sample collection mechanism collects a sample of the substance from the environment surrounding the IRAM unit and introduces the sample to the sample examination cassette. The sample examination cassette provides a platform for positioning and otherwise preparing the sample for investigation by the data collection mechanism, and for subsequent storage wherein the tested substances and images thereof are preserved for later removal from the IRAM unit for further testing or storage.

The data collection mechanism is adapted for collecting identifying information concerning the substance, with the information taking any one or more of a variety of forms, such as, for example, digital images, data points, test results, or sensor results. The data collection mechanism may include any one or more of the following: an imaging device for investigating solids or liquids; a mass spectrometer, gas chromatograph, or ion mobility spectrometer for investigating gases; a multiple reagent and sample treatment module; a radiation sensor; additional desired sensors or detection and identification mechanisms; a control module; and a processor and associated memory. Each IRAM unit may be individually configured as desired, particularly in light of any relevant considerations (e.g., needed capabilities, minimized cost). The aforementioned open architecture facilitates such customization.

The imaging device provides a digital image of the substance for comparison and analysis to identify solid or liquid substances. The imaging device may include, for example, a digital microscope; a visual camera; an infrared camera; or a thermal camera. The mass spectrometer, gas chromatograph, or ion mobility spectrometer provides spectrographic data points that can be used to identify gaseous substances.

The multiple reagent and sample treatment module allows for performing micro-chemical or biological testing and analysis of the substance in the sample examination cassette. More specifically, the sample treatment module allows for testing the substance by treating it with or exposing it to a variety of reagents, growth media, or other chemical or biological compounds wherein micro-amounts of the compounds are introduced to a micro-amount or micro-sample of the substance. Use of this feature, including introducing the compounds to the substance, may be remotely controlled by an operator of the OATS unit.

The radiation sensor monitors radiation levels, particularly changes in background radiation levels. The additional sensors or detection and identification mechanisms allow for including more specific testing capability as necessary or desired, thereby greatly enhancing the operational flexibility of the system.

The control module provides a mechanism and interface for the operator of the OATS unit to remotely control operation of the various components of the IRAM unit, particularly the imaging device and the sample treatment module. The processor and associated memory processes and stores data generated by other components of the IRAM unit, and facilitates communicating this data with the OATS unit. The temperature, wind direction/speed, and rain sensors monitor weather factors that may impact effectiveness, movement, and dissipation of many substances and that are useful in determining whether and how a substance may move or be moving within a geographic area. The transceiver provides encoded or encrypted two-way communication with the OATS unit. The power supply provides power to the other components of the IRAM unit. The local warning device allows for warning those in relatively close proximity to the IRAM unit, and therefore to the substance of interest, that a potentially dangerous condition exists.

Each IRAM unit is also preferably provided with a self-righting mechanism that substantially ensures that the IRAM unit will be properly oriented following deployment, particularly airborne deployment. Proper orientation is especially important to such functions as sample collection.

The OATS unit is adapted and operable to allow the operator thereof to remotely monitor and, when necessary or desired, control the IRAM units' activities; to perform image analysis on any images received from the IRAM units; and transmit reports on any detected substances of interest to the data processing and storage servers via the wide area telecommunications network. The OATS unit preferably includes one or more transceivers; a display; a processor and associated memory; a library or database of reference images of known substances; and image analysis and recognition software. The OATS unit may also include a position-determining mechanism.

The one or more transceivers allow for communicating with the IRAM units via a wireless or hardwired local area network and for communicating with the data processing and storage servers via the wide area telecommunications network. Preferably, the OATS unit includes at least two different types of transceiver devices in order to provide greater flexibility and choice in communications.

The display allows for viewing the data collected and transmitted by the IRAM units. The processor and associated memory control operation of other components and various functions of the OATS unit, including data processing and storage.

The library or database of reference images of known substances is stored in the memory associated with the processor, or, alternatively, may be accessed in whole or in part from a remote location via the transceiver. The image analysis and recognition software is stored in the memory and executed by the processor to compare the image generated by the imaging device with the reference images in the library. More specifically, the image analysis and recognition software compares or otherwise analyzes the generated image of the substance to determine which known substance the unidentified substance most resembles based upon such factors as, for example, color, shape, texture, brightness, color structure, and aspect ratio.

The position-determining mechanism allows the OATS unit to determine its own geographic position or location, particularly its position relative to the IRAM units.

The OATS unit preferably has access to a look-up table or other database of geographic locations associated with local reporting authorities and local reporting protocols or other policies. When data received from an IRAM unit indicates the presence of a threatening substance or other substance of interest, the geographic location of the particular IRAM unit, as determined by its onboard position-determining mechanism and transmitted to the OATS unit along with the collected data, is used in conjunction with the look-up table to identify proper local reporting authorities and policies. These authorities may, as appropriate, be notified directly to access and review the report stored on the data processing and storage servers.

The OATS units are also preferably adapted and operable to communicate and cooperate with each other and, as desired, with other computing resources in order to engage in or perform distributed or grid computing wherein an otherwise time-consuming processing problem (e.g., image comparison in order to identify the substance, or evaluation of multiple data sets from multiple IRAM units) is broken or partitioned into smaller problems or portions of problems that are processed substantially simultaneously and in parallel.

As mentioned, the report setting forth the collected data concerning the substance of interest is uploaded to the data processing and storage servers via the wide area network. Thereafter, the report can be accessed by any authorized person substantially anywhere in the world via the wide area network. Each such report preferably includes at least the relevant IRAM unit's geographic location coordinates; the time- and date-stamped digital image or other sensor data associated with the substance; and any other relevant information collected by the IRAM unit. The one or more data processing and storage servers may also be adapted to evaluate the data of the report in light of other considerations, including the data of other reports, in order to generate an overarching picture or perspective involving all available relevant data.

The hierarchy of response and evaluation authorities includes responsive entities and evaluative entities. The responsive entities may include, for example, local first responders; state or regional departments or agencies; and national departments or agencies such as the Department of Homeland Security or Federal Bureau of Investigation. The evaluative entities may include, for example, an overarching group of relevant experts with knowledge of such subjects such as, for example, medical issues relating to exposure to chemical, biological, or radioactive substances; legal, law enforcement, policy, or doctrinal issues; and historical cases, modeling, or simulation. Because the report is uploaded to the data processing and data storage servers and is thereafter accessible via the wide area network, the group of relevant experts may include substantially any experts or other appropriate persons located anywhere in the world. Advantageously, this allows for involving the most knowledgeable or otherwise best-choice experts without regard to their locations.

Thus, it will be appreciated that the system and method of the present invention provide a number of substantial advantages over the prior art, including, for example, providing a substantially automated and remotely controllable remote sensing unit that both allows for faster deployment and eliminates exposure risks to human operators. More specifically, the IRAM units can be temporarily deployed in any suitable manner (e.g., airdrop, balloon, robot) into an area to provide the quickest warning of the presence of a threatening substance. The IRAM units can also be permanently deployed, for example, in a single layer or concentric layers around a city to provide continuous monitoring and advance warning of a terrorist attack using weapons of mass destruction or other threatening substances. Such operational flexibility is not possible in the prior art, in part because a human operator must be outfitted and deployed with the prior art detection devices and because the prior art methods of testing and reporting are inefficient and time-consuming.

Furthermore, the open architecture of the IRAM unit allows for easy and convenient removal and replacement of malfunctioning or obsolete sensors, thereby reducing maintenance time and making the system more resistant to obsolescence. The open architecture also allows for an unprecedented degree of customizability to meet cost, capability, anticipated need, and other considerations.

Additionally, when the IRAM unit is equipped with the imaging device, the broadly capable image analysis and recognition technique of the present invention advantageously allows for more efficient, practical, and cost-effective monitoring and reporting than is possible with the substance-specific or interaction-intensive techniques used by the prior art.

Additionally, the feature of location self-awareness allows for faster notification of appropriate local authorities, and the feature of grid computing allows for cooperative processing resulting in much faster identification, evaluation, and response to potentially dangerous or deadly situations.

Additionally, the two or more types of transceivers on each OATS unit allow for greater communication flexibility and options during an emergency. More specifically, the preferred primary transceiver is used whenever possible and a secondary transceiver is used whenever necessary.

Additionally, by uploading reports describing the presence of a substance of interest into the one or more data processing and storage servers and establishing authorized access to the reports via the wide area network, the present invention makes possible the introduction and contribution of the group of relevant experts even though the group's members may be widely or even globally distributed.

These and other important features of the present invention are more fully described in the section titled DETAILED DESCRIPTION OF A PREFERRED EMBODIMENT, below.

BRIEF DESCRIPTION OF THE DRAWINGS

A preferred embodiment of the present invention is described in detail below with reference to the attached drawing figures, wherein.

DETAILED DESCRIPTION OF A PREFERRED EMBODIMENT

With reference to the figures, a system 10 and method is herein described, shown, and otherwise disclosed in accordance with a preferred embodiment of the present invention. Broadly, the present invention concerns a system 10 and method for identifying, reporting, and evaluating a presence of one or more solids, liquids, gases, or other substances of interest, particularly dangerous, hazardous, or otherwise threatening chemical, biological, or radioactive substances.

System

Figure 1:
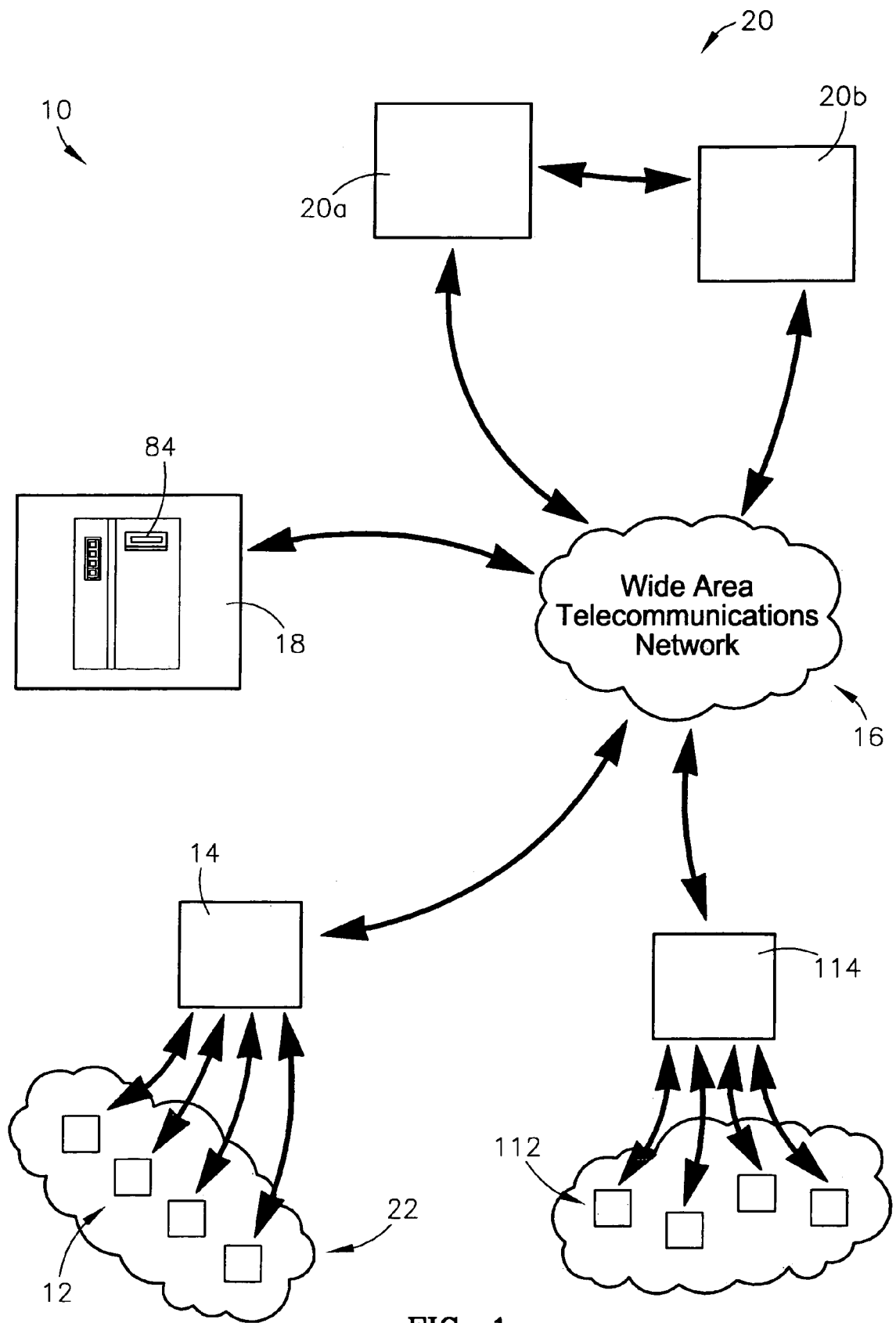
FIG. 1 is a block diagram of a system 10 for identifying, reporting, and evaluating a presence of a dangerous, hazardous or otherwise threatening solid, liquid, gas, or other substance, implemented in accordance with a preferred embodiment of the present invention.
Figure 2:
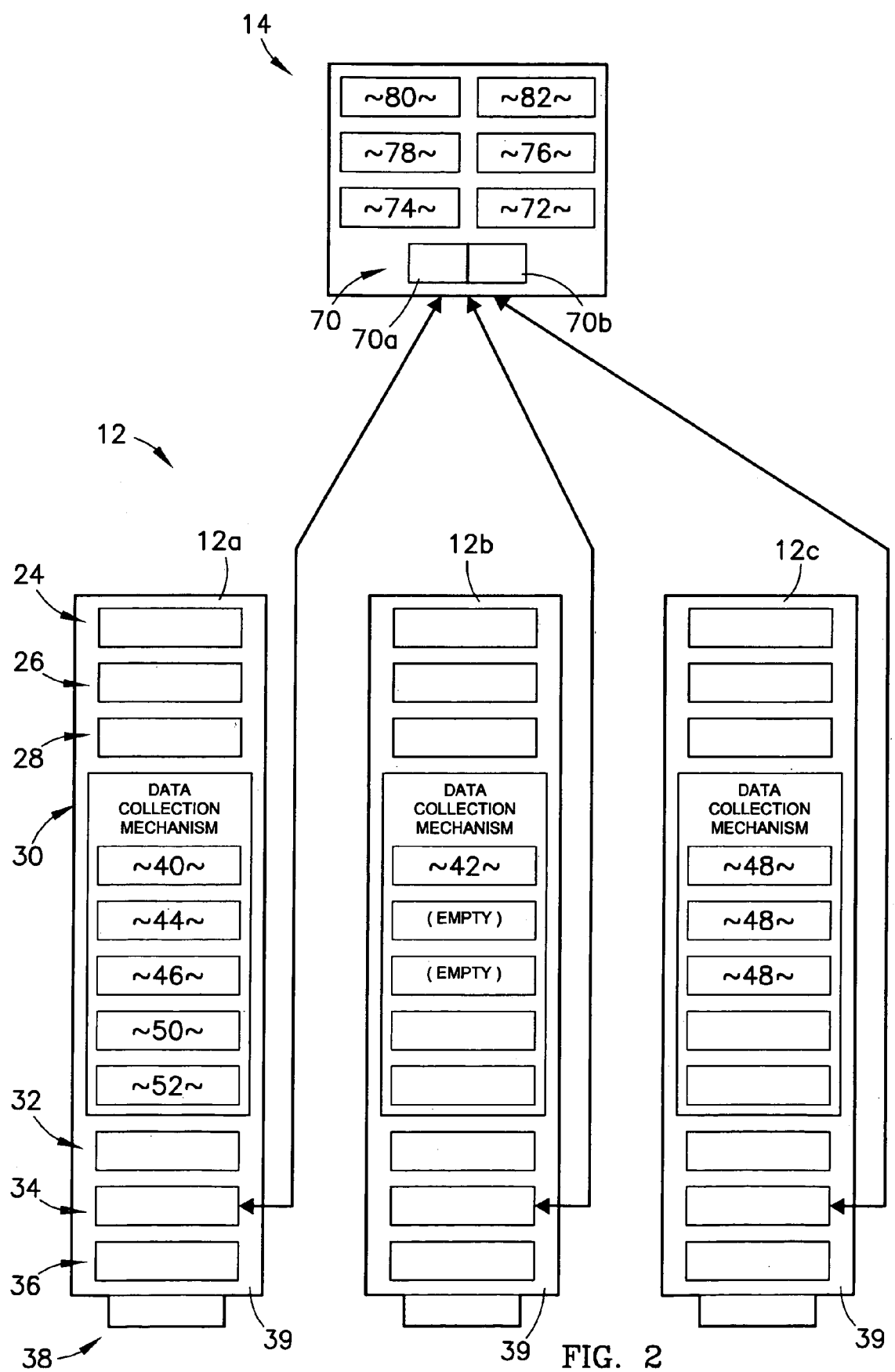
FIG. 2 is a block diagram showing elements of multiple IRAM units 12 and an OATS unit 14 which are components of the system 10 of FIG. 1.

Referring particularly to FIGS. 1 and 2, the system 10 broadly comprises one or more IRAM units 12; one or more OATS units 14; a wide area telecommunications network 16; and one or more remote data processing and storage servers 18. As discussed below, once the substance of interest is detected, the OATS unit 14 generates and uploads a report detailing its presence and other relevant information to the servers 18, whereafter the report is available for review by a hierarchy of response and evaluation authorities 20 via the wide area network 16.

Each IRAM unit 12 is adapted to substantially automatically and independently gather sensor and other data from within an area of interest 22 and communicate this data to the OATS unit 14. Each IRAM unit 12 preferably includes a position-determining mechanism 24; a sample collector mechanism 26; a sample examination cassette 28; a data collection mechanism 30 for collecting identifying and other relevant information concerning the substance; temperature, wind speed/direction, and rain sensors 32; a transceiver 34; a power supply 36; and a local warning device 38. The data collection mechanism 30 may include any one or more of the following: an imaging device 40 for investigating solids or liquids; a mass spectrometer 42, gas chromatograph, or ion mobility spectrometer for investigating gases; a multiple reagent and sample treatment module 44; a radiation sensor 46; additional relevant sensors or detection and identification mechanisms 48; a control module 50; and a processor 52 and associated memory. Substantially all of the aforementioned IRAM unit components are conventional, commonly available off-the-shelf devices. The IRAM unit 12 preferably uses an open architecture or interface from the IEEE 1451 family of intelligent sensor interfaces or an equivalent that allows for easily and conveniently removing and replacing the components (so called "plug-and-piay") without having to restart or reboot the IRAM unit 12 (so-called "hot-swapping"), thereby facilitating easy, convenient, and cost-effective removal and replacement of unneeded, malfunctioning, or obsolete components.

The position-determining mechanism 24 is preferably a global positioning system (GPS) receiver adapted to receive signals from a plurality of orbiting satellites and, based thereon, automatically and continually determine a particular geographic position or location of the IRAM unit 12. A suitable GPS receiver is available, for example, as the model GPS16 from Garmin International, Inc., which provides 12 satellite triangulation, WAAS capability, 3 meter accuracy, and an RS232 output. It will be appreciated that under some circumstances and in certain applications it is desirable to know the IRAM unit's position in greater detail, possibly including, for example, its directional orientation. Thus, the position-determining mechanism 24 may be adapted to provide such additional detail.

The sample collection mechanism 26 collects a sample of the substance from the environment 22 surrounding the IRAM unit 12. The collection mechanism 26 may include an extendable arm-type collection component for collecting samples of solids, a pump-based suction-type collection component for collecting samples of liquid or gaseous substances, any combination thereof, or any other desired collection component using any suitable collection technique. The collected sample is introduced to the sample examination cassette 28.

Figure 3:
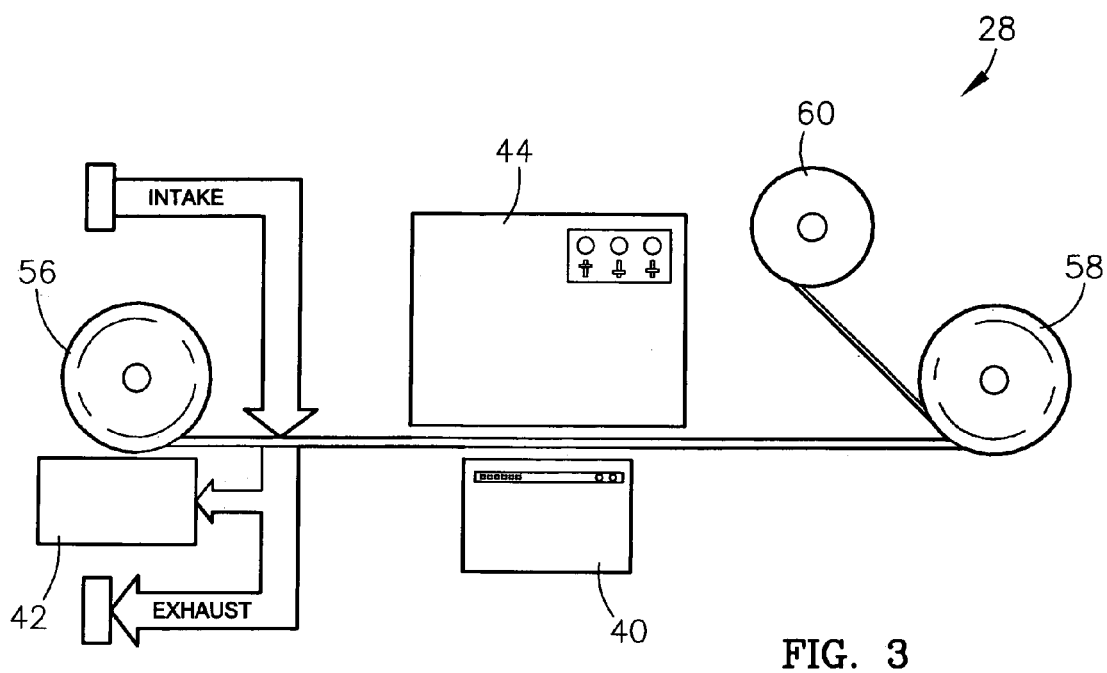
FIG. 3 is a block diagram showing the interrelation of elements of a sample examination cassette 28 which is a component of the system 10 of FIG. 1.

Referring also to FIG. 3, the sample examination cassette 28 provides a platform for positioning and otherwise preparing the sample of the substance for investigation by the data collection mechanism 30, and for subsequent storage. The cassette 28 includes a roll of filter paper 56 and an archive spool 58. Where the data collection mechanism 30 includes the imaging device 40 (described below), the cassette will also preferably include a roll of film 60 or other medium providing an impermeable barrier for separating and isolating the various samples of substances. The roll of filter paper 56 is a roll of sample collection and reagent HEPA filter paper media mounted on a first spool and onto which the sample collection mechanism 26 deposits the sample. The roll of film 60 is mounted on a second spool and covers the filter paper as it is wound upon the archive spool 58. The archive spool 58 collects and stores the advancing rolls of filter paper 56 and film 60 so that the tested substances are preserved for later removal from the IRAM unit 12 and further testing or storage.

Figure 3A:
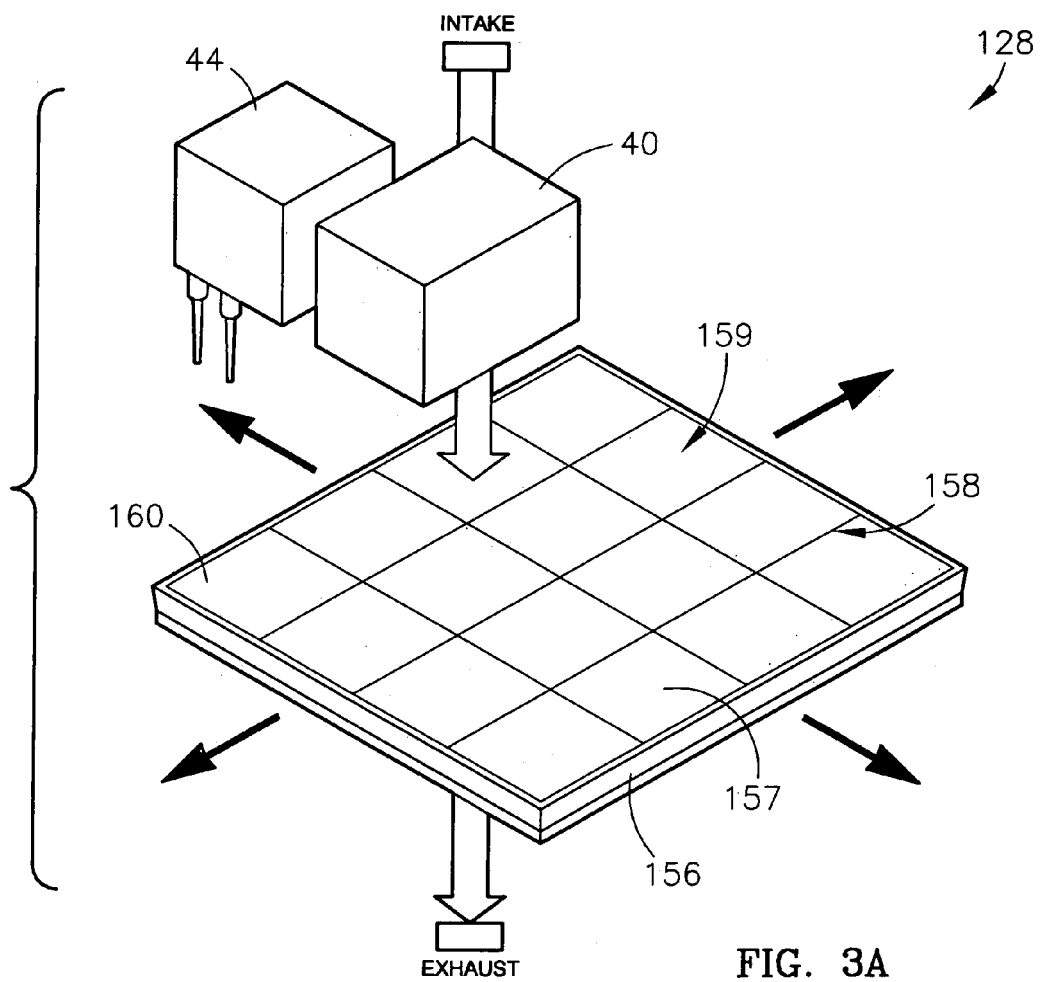
FIG. 3A is a block diagram showing the interrelation of elements of an alternative embodiment of the sample examination cassette 128 which is a component of the system 10 of FIG. 1.

Referring also to FIG. 3A, an alternative embodiment of the sample examination cassette 128 is shown including a movable stage 156; a sheet of the filter paper 157; and a superimposed grid 158. The sheet of filter paper 157 is placed upon the movable stage 156 and a vacuum used to hold it in place, then the grid 158 is superimposed upon the filter paper 157 so as to define a plurality of sample areas 159 and a reserved area 160. In use, the stage 156 moves (by, e.g., stepper motors) relative to the sample collection mechanism 26 so that the sample is introduced to or deposited within a particular sample area defined by the grid 158. No sample is ever introduced to the reserved area 160 because that location corresponds to the sample treatment module 44. The stage 156 then moves so as to position the particular sample area and the substance located therein before the imaging device 40 or, if testing is desired, before the sample treatment module 44. This process is repeated for each sample of each substance until the plurality of sample areas 159 are full. Thereafter, the sheet of filter paper 157 may be removed for further testing or storage. It will be appreciated that this alternative embodiment eliminates the roll of film 60 and the archive spool 58 of the previously-described embodiment.

The data collection mechanism 30 is adapted for collecting identifying information concerning the substance. This information may take any one or more of a variety of forms, including, for example, digital images, data points, test results, or sensor results. As mentioned, the data collection mechanism 30 may include any one or more of the following: an imaging device 40 for investigating solids or liquids; a mass spectrometer 42, gas chromatograph, or ion mobility spectrometer for investigating gases; a multiple reagent and sample treatment module 44; a radiation sensor 46; additional desired sensors or detection and identification mechanisms 48; a control module 50; and a processor 52 and associated memory. As shown in FIG. 2, each IRAM unit 12 may be individually configured as desired, particularly in light of any relevant considerations (e.g., needed capabilities, minimized cost). For example, a first IRAM unit 12a is shown equipped with the imaging device 40, the sample treatment module 44, and the radiation sensor 46; a second IRAM unit 12b is shown equipped with the mass spectrometer 42; and a third IRAM unit 12c is shown equipped with other desired sensors 48. The aforementioned open architecture facilitates such customization.

The imaging device 40 provides a digital image of the substance for comparison and analysis to identify solid or liquid substances. The imaging device 40 may include a digital microscope adapted to provide highly-magnified LIVE images and SNAP capture capabilities and to output in a .tif or other standard format. A suitable digital microscope is available, for example, as the model VL-S from Scalar Corporation, which provides 1× to 400× magnification, color images, and S-video output.

Alternatively, the imaging device 40 may include any of a variety of image capturing cameras, such as, for example, visual cameras; infrared cameras; or thermal cameras, all of which generate images that can be analyzed using the image analysis and recognition techniques discussed below. It will be appreciated that these image capturing cameras are more suited for identifying objects or persons than biological, chemical, or radioactive substances. It is contemplated that the present invention can also be used to remotely locate or identify objects or persons. For example, the IRAM unit 12 could be made mobile and used by firefighters to investigate burning or smoke filled areas for trapped persons. In another example, the IRAM unit 12 could be deployed about an event or location to identify terrorists, criminals, or other persons using facial recognition or other identification techniques.

The mass spectrometer 42, gas chromatograph, or ion mobility spectrometer provides spectrographic data points that can be used to identify gaseous substances. A suitable ion mobility spectrometer is available, for example, as the model APD2000 from Smiths Detection, which is operable to detect such chemical substances as, for example, GA, GB, GD, VX, HD, HN, lewisite, pepper spray, and mace. Alternatively, the mass spectrometer 42 or other similar device may provide a digital image of the spectrograph of the substance for comparison analysis in a manner similar to the digital image generated by the imaging device 40 described above.

The multiple reagent and sample treatment module 44 allows for performing micro-chemical or biological testing and analysis of the substance in the sample examination cassette 28. More specifically, the sample treatment module 44 allows for testing the substance by treating it with or exposing it to a variety of reagents, growth media, or other chemical or biological compounds wherein micro-amounts of the compounds are introduced to a micro-amount or micro-sample of the substance. If the IRAM unit 12 is also equipped with the aforementioned imaging device 40, then this process of testing and analysis and any results thereof may be viewable in real-time. Preferably, a number of such micro-chemical or biological tests are performed substantially simultaneously, with micro-amounts of multiple compounds being simultaneously introduced to multiple micro-samples of the substance, wherein the imaging device 40 moves over the samples or the samples move relative the imaging device 40 in order to provide images of each of the simultaneously-occurring tests. Use of this feature, including introducing the compounds to the substance, may be remotely controlled by an operator of the OATS unit 14.

The radiation sensor 46 monitors radiation levels, particularly changes in background radiation levels. A suitable radiation monitor is available, for example, as the model RAM R200 from Rotem Industries, Inc., which measures between 10 μR/h and 100 R/hour and provides an RS232 output.

The additional sensors or detection and identification mechanisms 48 allow for including more specific testing capability as necessary or desired. This capability may be stand-alone as in the third IRAM unit 12c, or may, for example, be used to supplement the images generated by the imaging device 40. The additional sensors or mechanisms 48 may include, for example, GC/MS sensors, chemical sensors, biological sensors, acoustic sensors, visual sensors, movement sensors, seismic sensors, magnetic sensors, or solar sensors.

The control module 50 provides a mechanism and interface for the operator of the OATS unit 14 to remotely control operation of the various components of the IRAM unit 12, particularly the imaging device 40 and the sample treatment module 44. The capabilities of the control module 50 will depend heavily on the nature and capabilities of the components being controlled. In the case of a digital microscope, for example, the control module 50 may allow the operator to adjust magnification, field of view, and focus using one or more stepper motors. A suitable control module is available, for example, as the model PCI/2-8×1 switch module from Cytec Corporation, which provides DB-37 pin output.

The processor 52 and associated memory processes and stores data generated by the other components of the IRAM unit 12, and facilitates communicating this data with the OATS unit 14. The processor 52 may use any suitable operating system, such as, for example, the Windows 98SE operating system available from Microsoft Corp., and may be provided with a USB/RS232 converter for interfacing or facilitating communication with other components of the IRAM unit 12. A suitable converter that provides up to four channels for sensors is available, for example, as the model USB232/4 from National Instruments. The processor 52 is also adapted and operable to perform various other necessary onboard operating functions, including, for example, calibrating, integrating, and otherwise managing the various sensors, transducers, and other components, and collecting samples using the sample collection mechanism 26.

The temperature, wind direction/speed, and rain sensors 32 monitor potentially relevant weather factors that may impact effectiveness, movement, or dissipation of many substances and that are useful in determining whether and how a substance may move or be moving within a geographic area. High or low temperatures, for example, may deactivate certain threatening chemicals; winds may spread or dissipate threatening gases; rain may dilute or destroy threatening powders or introduce threatening liquids into water supplies. A suitable weather station is available, for example, from Texas Weather Instruments, Inc., which provides temperature, wind direction/speed, and rain sensing capabilities and a DDE-link output.

The transceiver 34 provides encoded or encrypted two-way communication with the OATS unit 14. Data collected by the data collection mechanism 30, for example, is transferred as simple batch files using Secure Socket Layer (SSL) with 1024 bit encryption. Control signals from the OATS unit 14 to the control module 50 or processor 52 are also communicated in this manner. As desired, each IRAM unit 12 may include more than one transceiver, type of transceiver, or type of communications mode in order to provide greater flexibility and choice in communications. The transceiver device 34 preferably makes use of a wireless LAN Ethernet link using any appropriate IEEE 802-family standard. A suitable wireless Ethernet link may be implemented using, for example, the model BEFW11S4 router from Linksys, providing four channel access points and 2.4 GHz using the IEEE 802.11b standard. Unfortunately, wireless communication is not always practical, may be jammed, or be otherwise unusable (e.g., due to interference). For example, the IRAM unit 12 may be deployed into an artificial structure, underground, or other area where wireless communications are naturally or artificially inhibited. Thus, provision is preferably made for attaching a communications cable (e.g., Ethernet cable connection) to the IRAM unit 12 to allow for a hardwired LAN Ethernet link when necessary or desirable.

The power supply 36 provides power to the other components of the IRAM unit 12. A suitable power supply is available, for example, as the model LPQ-112 power supply from Astec Power. It is also contemplated that the power supply 36 could be a hydrogen fuel cell or variation thereof. Furthermore, where the IRAM unit's location is fixed, such as when permanently positioned around or within a city, the primary power supply 36 may be a hardwired connection to a reliable, permanent power supply, possibly supplemented or backed-up by a battery, hydrogen fuel cell, or other secondary self-contained power supply.

The local warning device 38 allows for warning those in relatively close proximity to the IRAM unit 12, and therefore to the substance of interest, that a potentially dangerous condition exists. The local warning device 38 can be activated by any onboard sensor or detection device able to make a positive identification of the substance (e.g., the radiation sensor 46 or other specialized sensor or detector 48). The local warning device 38 may take the form of any device, such as, for example, a horn, siren, or flashing light, adapted and operable to provide a significant audible or visual warning.

Preferably, at least any sensitive component or portion of the IRAM unit 12 is substantially surrounded with a protective potting or hardening material 39. The nature of the material 39 will depend upon the nature of the sensitivity. For example, an impact-sensitive component may be substantially surrounded by a cushioning expandable foam or by cushioning micro-capsules; a temperature-sensitive component may be substantially surrounded by an insulative material; and a tamper-sensitive component may be substantially surrounded by a material that inhibits or prevents physical or other access to the component.

Self-Righting Mechanism

Figure 4:
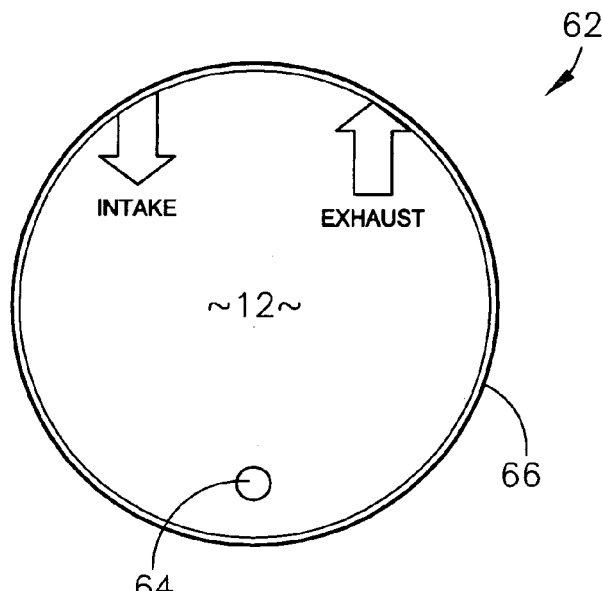
FIG. 4 is a depiction of a self-righting mechanism 62 which is a component of the IRAM unit 12 of the system 10 of FIG. 1.

Referring also to FIG. 4, each IRAM unit 12 is preferably provided with a self-righting mechanism 62 that substantially ensures that the IRAM unit 12 will be properly oriented following deployment, particularly airborne deployment. Proper orientation may be especially important to such functions as sample collection. One possible self-righting mechanism 62 involves giving the IRAM unit 12 a substantially spherical form and offsetting its center of gravity 64 appropriately apart from one or more inlet and outlet ports associated with the sample collection mechanism 26. If the IRAM unit 12 lands or otherwise finds itself in an improper orientation, the spherical shape causes the IRAM unit 12 to roll until the center of gravity 64 is located as low as possible, thereby orienting the IRAM unit 12 so as to properly position its intake and exhaust ports for operation. The spherical shape may be a fixed feature or, alternatively, may be the result of an inflatable balloon 66 or balloon-like structure that, when deflated, allows for storing the IRAM unit 12 in a more efficient rectangular shape prior to deployment, and, when inflated, allows for assuming the self-righting spherical shape during or after deployment.

OATS Unit

The OATS unit 14 is adapted and operable to allow the operator thereof to remotely monitor and, when necessary or desired, control the IRAM units' activities; to perform image analysis on any images received from the IRAM units 12; and transmit reports on any detected substances of interest to the data processing and storage servers 18 via the wide area telecommunications network 16.

The OATS unit 14 preferably includes one or more transceivers 70; a display 72; a processor 74 and associated memory; a library 76 or database of reference images of known substances; and image analysis and recognition software 78. The OATS unit 14 may also include a position-determining mechanism 80.

The one or more transceivers 56 allow for communicating with the IRAM units 12 via a wireless or hardwired local area network and for communicating with the data processing and storage servers 18 via the wide area telecommunications network 16. Preferably, the OATS unit 14 includes at least two different types of transceiver devices in order to provide greater flexibility and choice in communications. A primary transceiver device 70a may, for example, be adapted for wireless cellular telephone communication that allows for relatively inexpensive, omnidirectional, and high-bandwidth communication. Unfortunately, such wireless services are not available everywhere or may exceed capacity and jam or be otherwise unusable (e.g., due to interference) during an emergency. Thus, a secondary transceiver device 70b may, for example, be a satellite phone link that is more widely available and usable during an emergency.

In more detail, the OATS unit 14 communicates with the IRAM units 12 using wireless DHCP LAN addressing and encryption; while the OATS unit 14 uploads data to the data processing and storage servers 18 and communicates with external parties and agencies using TCP/IP WAN domains, addressing, SSL (128 bit minimum) encoding, and digital certificates. As desired, other suitable data scrambling schemes may be used, such as, for example, SSH or WEP. Encoding may be sufficient for communicating information that is unclassified but sensitive; encryption may be used where greater security is required or desired. The wide area network may be, for example, the Internet, which is particularly suitable for civilian use, or a more secure, limited access network, which is more suitable for military or other government use.

The display 72 allows for viewing the data collected and transmitted by the IRAM units 12. The OATS unit 14 preferably provides a LabVIEW-based or similar user interface for display on the display 72 and adapted to communicate the received data to the operator of the OATS unit 14 and to facilitate monitoring and controlling the IRAM unit's various functions, including, for example, controlling pan, zoom, and other functions of the imaging device 40; monitoring and controlling activities of the sample treatment module 44; viewing the location coordinates of the IRAM unit 12 as generated by the IRAM unit's position determining mechanism 24; and viewing the digital image or other data generated or collected by the data collection mechanism 30 and various other sensors or detectors. The user interface also preferably provides for initiating or viewing results of system diagnostics to ensure and maintain adequate sensing and control. The user interface also preferably facilitates uploading reports to the data processing and storage servers 18 for storage and subsequent review via the wide area network 16 by any authorized person substantially anywhere in the world.

The processor 74 and associated memory control operation of other components and various functions of the OATS unit 14, including data processing and storage. The processor 74 may be provided with any suitable operating system, such as, for example, the Linux version 7.0 operating system available from Red Hat, Inc., or the Windows 2000 operating system available from Microsoft Corp.

The library 76 or database of reference images of known substances is stored in the memory associated with the processor 74 or, alternatively, may be accessed in whole or in part from a remote location via the transceiver 70. The image analysis and recognition software 78 is stored in the memory and executed by the processor 74 to compare the image generated by the imaging device 40 with the reference images in the library 76. More specifically, the image analysis and recognition software 78 is adapted to access the reference images and compare or otherwise analyze the generated image of the substance to determine which known substance the unidentified substance most resembles. The image analysis and recognition software 78 compares the generated image with the reference images based upon such factors as, for example, color, shape, texture, brightness, color structure, and aspect ratio. It is possible that no exact match will be made, and instead a number of reference images will be identified as closely matching the generated image. Preferably, the reference images are provided with a threat indicator to quickly communicate their threat potential. In one implementation, for example, the threat indicator takes the form of a red, yellow, or green border surrounding each reference image, wherein red indicates a hazardous substance or high threat, yellow indicates a questionable substance or possible threat, and green indicates low or no threat, thereby allowing for quick determination of the threat level posed by a particular substance. The image analysis and recognition software 78 may, as desired, be calibrated periodically using one or more calibration/standardization images of known substances which may also be stored in the library 76.

As mentioned, the present invention can also be adapted to identify or locate objects or persons. Thus, the preferred image analysis and recognition software 78 is broadly capable of identifying substances, objects, and persons, as desired, given the image generated by the IRAM unit 12. For example, the image analysis and recognition software 78 is preferably capable of or adaptable so as to be capable of recognizing facial or other bodily characteristics, thereby allowing for identifying persons of interest.

The position-determining mechanism 82 allows the OATS unit 14 to determine its own geographic position or location, particularly its position relative to the IRAM units 12.

Location Self-Awareness Feature

The OATS unit 14 preferably has access to a look-up table 82 or other database of geographic locations associated with local reporting authorities (e.g., police departments, sheriff departments, fire departments, elected officials, other first responders) and local reporting protocols or other policies.

The look-up table 82 may be stored on the memory associated with the processor 74 or may be accessed from a remote location via the transceiver 70.

When data received from an IRAM unit 12 indicates the presence of a threatening substance or other substance of interest, the geographic location of the particular IRAM unit 12, as determined by its onboard position-determining mechanism 24 and transmitted to the OATS unit 14 along with the collected data, is used in conjunction with the look-up table 82 to identify proper local reporting authorities and reporting protocols and other policies. These authorities may, as appropriate, be notified directly (e.g., via electronic mail, telephone, or pager) to access and review the report stored on the data processing and storage servers 18 via the wide area network 16.

Thus, prior art failings with regard to both timely dissemination of correct information and compliance with local reporting protocols and other policies are advantageously overcome.

Grid Computing Feature

The OATS units 14 are preferably adapted and operable to communicate and cooperate with each other and, as desired, with other computing resources in order to engage in or perform distributed or grid computing wherein an otherwise time-consuming processing problem (e.g., image comparison in order to identify the substance) is broken or partitioned into smaller problems or portions of problems that are processed substantially simultaneously and in parallel. The results of the processing of these smaller problems or portions of problems are subsequently combined or otherwise integrated to arrive at a result for the larger, more complex problem. Though the broad concept of grid computing is known in the prior art, and appropriate software exists or can be readily generated by one with ordinary skill in the art of computer programming, the use of grid computing is unknown in the field-testing equipment to which the present invention relates.

Additionally or alternatively, the IRAM units 12 may engage in or perform grid computing. It should be noted that, preferably, the IRAM units 12 do not communicate directly with one another. Instead, such communication is facilitated by and only occurs through the OATS unit 14. Alternatively, the system 10 may be implemented to allow the IRAM units 12 to communicate independent of the OATS unit 14, particularly when communicating about such matters as grid computing.

Servers

As mentioned, the report setting forth collected data concerning the substance of interest is uploaded to the data processing and storage servers 18 via the wide area network 16. Thereafter, the report can be accessed by any authorized person substantially anywhere in the world via the wide area network 16. Each such report preferably includes at least the reporting IRAM unit's geographic location coordinates; the time- and date-stamped digital image or other sensor data associated with the tested substance; and any other relevant information collected by the IRAM unit 12.

The one or more data processing and storage servers 18 may be provided with and employ artificial intelligence or similar logic or other evaluative software 84 to evaluate the data of the report in light of other considerations, including the data of other reports. In this manner, though each OATS unit 14 knows only of the data collected by its own IRAM units 12, an overarching picture or perspective involving all available relevant data can be created and evaluated. Such large scale evaluation may, for example, involve plume or other downwind hazard prediction software models or vector software models or simulations. The data processing and storage servers 18 may engage in or perform grid computing (in the manner described above) in order to more quickly and efficiently conduct the aforementioned large scale evaluation.

The data processing and storage servers 18 are preferably mirrored to assure data security and reliability.

System Access Management Scheme

It will be appreciated that electronic mail and similar communication mechanisms suffer from a number of disadvantages that make them unsuitable for use in disseminating or making available the reports generated by the present invention. More specifically, electronic mail technologies are point-to-point in nature with no managed, permanent, and shared repository of enterprise-wide program knowledge. There is little or no security, and "need-to-know" control is managed informally by each user. Furthermore, electronic mail technologies typically cannot exchange or cannot efficiently exchange large (10 Mbytes or greater) attachments.

Thus, the data processing and storage servers 18 preferably provide a network-based multi-point repository service having an adequate control environment to ensure that need-to-know control is properly managed, even for unclassified non-sensitive information pools. This file-sharing system should support administration and information management functions such as, for example, back-up recovery; audit trails; and full interoperation with standard enterprise desktop and operating environments with little or no software installation, maintenance, or costs required. The file-sharing system should also include a searchable and administrated meta-data structure to allow users to navigate the enterprise's shared and growing information pool. Additionally, the file-sharing system should support existing standard electronic mail and web browser technology without requiring any software modules, plugins, or other modifications to the users' equipment.

Preferably, a user interface in the form of a website hosted by the data processing and storage servers 18 is developed that both supports a process whereby new users can gain initial access to and existing users can navigate through the stored reports.

Gaining initial access to the file-sharing system and the reports stored therein preferably involves a voucher mechanism whereby an existing user or other authorized person (e.g., project supervisor) is contacted and communicated with directly (not via, e.g., electronic or voice mail) to vouch for the new user requesting initial access. The vouching person also indicates the types of information that the new user has a need to know. One or more initial passwords will be provided to the new user, preferably by a secure communication medium, but the initial passwords must be changed once the user has successfully used them to access the website for the first time. Furthermore, it may be required that the passwords be changed periodically. Separate directories may be provided for each level of the hierarchy of authorities (e.g., local, state, regional, national) to facilitate efficient navigation.

As mentioned, when a report is uploaded, appropriate members of the hierarchy of authorities may be notified using any practical mechanism of the need to login to the data processing and storage servers 18 and view the particular report.

Hierarchy of Response and Evaluation Authorities

As mentioned, the present invention contemplates a hierarchy of response and evaluation authorities 20, including responsive entities 20a and evaluative entities 20b. The responsive entities 20a may include, for example, such as local (e.g., city or county) first responders (e.g., police, firefighters, emergency medical services); state or regional departments or agencies; national departments or agencies such as the Department of Homeland Security or Federal Bureau of Investigation. The evaluative entities 20b may include, for example, an overarching group of relevant experts on subjects such as, for example, medical issues relating to exposure to chemical, biological, or radioactive substances; legal, law enforcement, policy, or doctrinal issues; and historical cases, modeling, or simulation.

Also as mentioned, the location self-awareness feature of the IRAM units 12 and OATS unit 14 allows for associating GPS-determined geographic locations of substances of interest with specific contact information and specific policies and protocols for appropriate local authorities. Thus, for example, city A may require that a particular HAZMAT responder or team of HAZMAT responders be notified first of any detection of hazardous substances, while county B may require that the county sheriff's office and county health department both be notified first. Given the above-described look-up table 82, the OATS unit 14 need only receive and look-up the geographic location of the detecting IRAM unit 12 to match the location to the proper authority and policy, and implement the policy by notifying the appropriate authorities of the detection and request that they access the one or more processing and data storage servers 18 to view the full report. A default policy may be provided for authorities who have no specific requirements.

Because the report is uploaded to the data processing and data storage servers 18 and is thereafter accessible via the wide area network 16, the group of relevant experts 20b may include substantially any experts or other appropriate persons located anywhere in the world. Advantageously, this allows for involving the most knowledgeable or otherwise best-choice experts without regard to their locations. The experts have full access to the report data, including the image generated by the imaging device 40, any results generated by the sample treatment module 44, and other sensor data.

EXAMPLE

It will be appreciated that the system 10 of the present invention may be adapted for use in any number of applications, such as, for example, monitoring hazardous industrial pollutants; monitoring agricultural or manufacturing areas for beneficial or harmful substances; detecting acts of terrorism involving nuclear, biological, or chemical weapons; monitoring battlefields or other hostile areas; or monitoring suspect or sensitive areas for intelligence gathering purposes.

Figure 5:
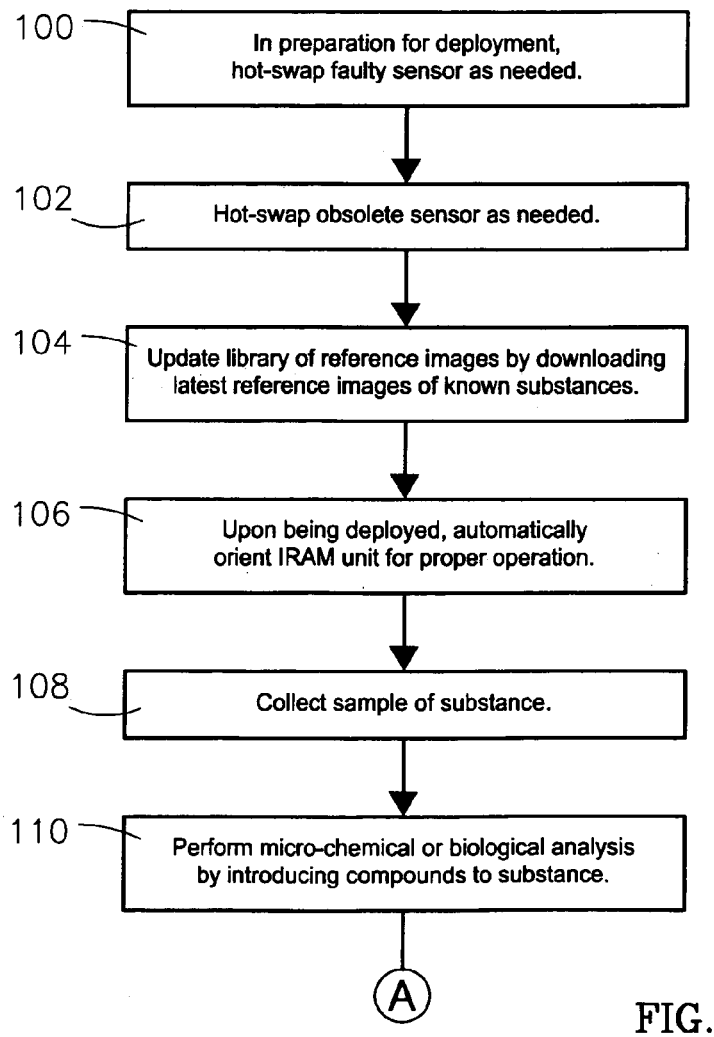
FIG. 5 is a first portion of a flowchart of steps involved in practicing the present invention.
Figure 6:
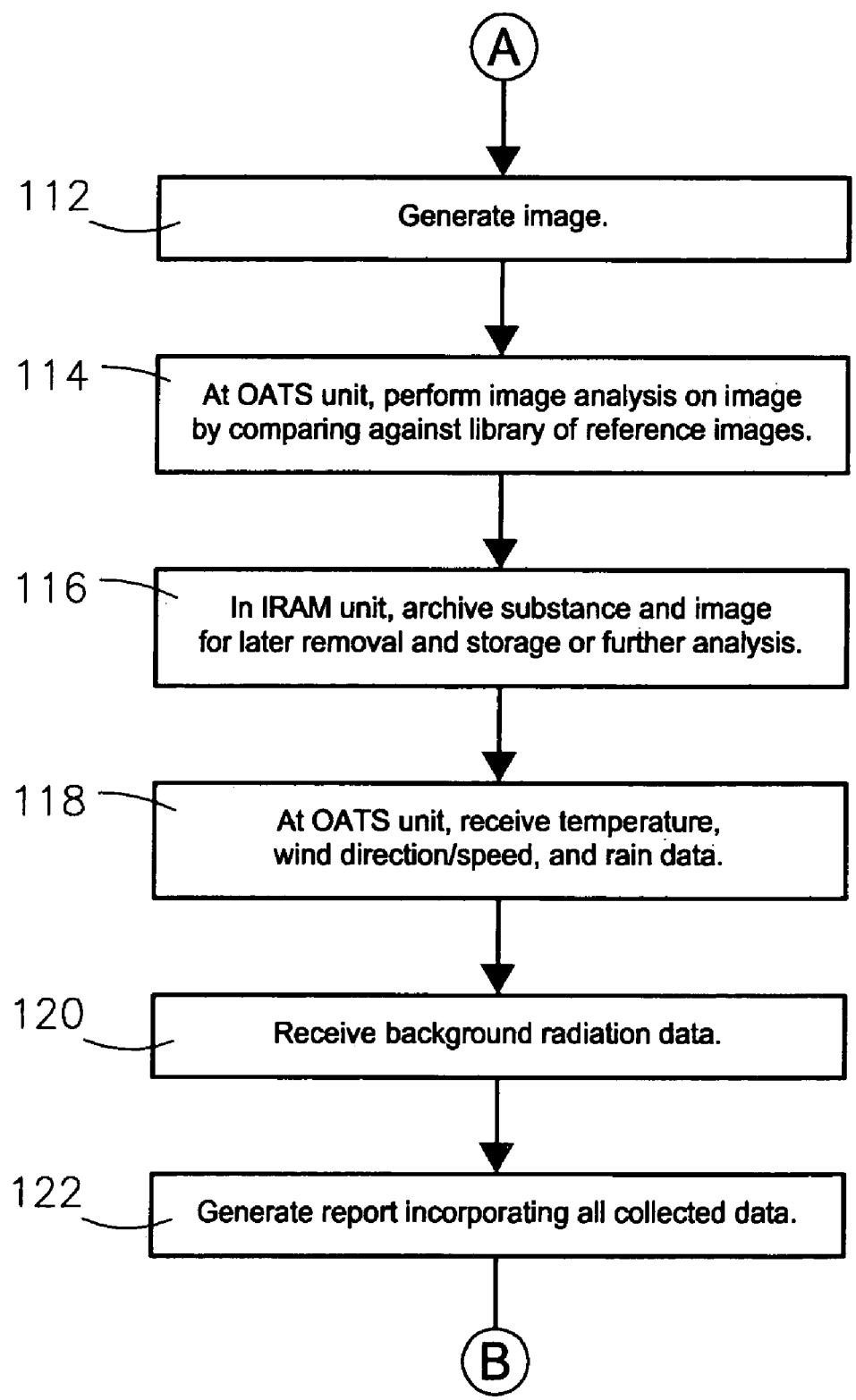
FIG. 6 is a second portion of the flowchart beginning in FIG. 5.
Figure 7:
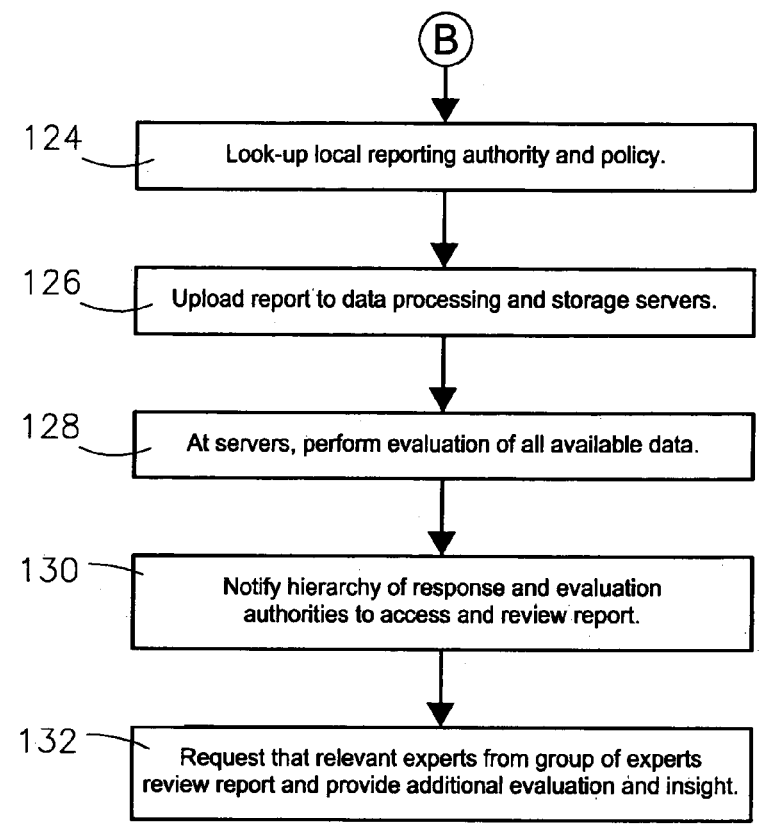
FIG. 7 is a third portion of the flowchart beginning in FIG. 5.

In an illustrative example of use and operation, the system 10 of the present invention may function as follows. Referring particularly to FIGS. 5–7, in response to a spill or leak of hazardous or threatening substances, multiple IRAM units 12 are prepared to be airdropped into the surrounding area to confirm the presence of the substances and extent of contamination. In the process of this deployment, a needed sensor in one of the IRAM units 12 is diagnosed as faulty. The faulty sensor is removed and a replacement installed in seconds, as depicted in box 100, thanks to the IRAM unit's open architecture and ability to "hot swap" sensors without rebooting. Similarly, an operational but obsolete sensor is equally easily removed and replaced, as depicted in box 102. In order to ensure the most up-to-date information, the library 76 of reference images is updated by downloading the latest reference images of known substances, as depicted in box 104.

Upon being airdropped and hitting the ground, the self-righting mechanism 62 activates or otherwise acts to properly orient each IRAM unit 12, as depicted in box 106. The sample collection mechanism 26 collects a sample of a substance to be identified and deposits it onto the roll of filter paper 46 within the sample examination cassette 28, as depicted in box 108. The sample treatment module 44 automatically or under direction of the operator of the OATS unit 14 introduces any reagents, growth media, or other compounds or otherwise performs any desired chemical or biological testing on the sample, as depicted in box 110. The imaging device 40 then generates a digital image of the suspect solid or liquid, as depicted in box 112. This image is transmitted to the OATS unit 14 where the image analysis and recognition software 78 compares or otherwise analyzes the image against the library 76 of reference images, as depicted in box 114.

If the image of the substance does not exactly match any particular reference image in the library 76, but does match, within a pre-established margin of error, a number of reference images, the OATS unit 14 may arrange the closest matching reference images from best to worst and present these to the operator of the OATS unit 14 or other authority for further analysis. Alternatively or additionally, the image analysis and recognition software 78 may allow for assigning a probability or determining a degree to which the generated digital image of the substance matches the one or more closest reference images, and reporting such.

Once the substance is identified, the filter paper 56 on which the tested sample of the substance resides and the roll of film 60 providing an impermeable barrier for isolating the substance are rolled onto the archive spool 58 for later removal and possible further analysis or storage, as depicted in box 116. The temperature, wind direction/speed, and rain sensors 32 provide weather information relevant to movement or dispersal of or otherwise affecting any threatening substance, as depicted in box 118. The radiation sensor 46 detects any change in background radiation, as depicted in box 120. This information is transmitted to the OATS unit 14.

The OATS unit 14 then generates a report incorporating all of this information, as depicted in box 122. The report may include the generated image of the substance and the matching or closely matching reference image(s); the IRAM unit's geographic location as determined by the onboard position determining mechanism 24; a probability reflecting the degree of confidence that the match is correct such that the substance has been correctly identified; and all other sensor data.

If the generated image of the substance matches a reference image of a threatening substance, then the OATS unit processor 74 accesses the look-up table 82 of local authorities and policies or protocols. An appropriate local authority and policy or protocol is identified from the look-up table 82 based upon the detecting IRAM unit's geographic location, as depicted in box 124. If no particular authority or policy or protocol is specified for the particular location, a default is used. Policy and protocol information may include when or under what circumstances to report; whom to report to; and in what form or how to report. If appropriate, the local authority is notified to access and review the report. The primary transceiver 70*a* of the OATS unit 14 communicates and uploads the report to the data processing and storage servers 18, as depicted in box 126. All such communication is appropriately encoded.

The one or more data processing and storage servers 18 may gather the report, other reports from other OATS units 14, and other relevant data, and input this information into appropriate artificial intelligence or other software tools to provide a broad evaluative overview or perspective of the situation, as depicted in box 128.

Depending on the nature of the identified substance, the particular circumstances surrounding its presence, and established protocols, appropriate authorities may be notified to access the one or more data processing and storage servers 18 in order to review the report, as depicted in box 130. Such notification may be accomplished using any conventional mechanism.

An agency in the hierarchy of response and evaluation authorities 20 requests that particular, relevant experts from the group of experts review the report and provide additional evaluation and insight, as depicted in box 132. The particular experts are widely distributed across the globe, but are able to quickly access and review the report via the Internet 16.

Advantages

From the preceding description it will be appreciated that the system and method of the present invention provide a number of substantial advantages over the prior art, including, for example, providing a substantially automated and remotely controllable remote sensing unit that both allows for faster deployment and eliminates exposure risks to human operators. More specifically, the IRAM units can be temporarily deployed in any suitable manner (e.g., airdrop, balloon, robot) into an area to provide the quickest warning of the presence of a threatening substance. The IRAM units can also be permanently deployed, for example, in a single layer or concentric layers around a city to provide continuous monitoring and advance warning of a terrorist attack using weapons of mass destruction or other threatening substances. Such operational flexibility is not possible in the prior art, in part because a human operator must be outfitted and deployed with the testing equipment and because the prior art methods of testing and reporting are inefficient and time-consuming.

Furthermore, the open architecture of the IRAM unit allows for easy and convenient removal and replacement of malfunctioning or obsolete sensors, thereby reducing maintenance time and making the system more resistant to obsolescence. The open architecture also allows for an unprecedented degree of customizability to meet cost, capability, anticipated need, and other considerations.

Additionally, when the IRAM unit is equipped with the imaging device, the broadly capable image analysis and recognition technique of the present invention advantageously allows for more efficient, practical, and cost-effective monitoring and reporting than is possible with the substance-specific or interaction-intensive techniques used by the prior art.

Additionally, the feature of location self-awareness allows for faster notification of appropriate local authorities, and the feature of grid computing allows for cooperative processing resulting in much faster identification, evaluation, and response to potentially dangerous or deadly situations.

Additionally, the two or more types of transceivers on each OATS unit allow for greater communication flexibility and options during an emergency. More specifically, the preferred primary transceiver is used whenever possible and a secondary transceiver is used whenever necessary.

Additionally, by uploading reports describing the presence of a substance of interest into the one or more data processing and storage servers and establishing authorized access to the reports via the wide area network, the present invention makes possible the introduction and contribution of the group of relevant experts even though the group's members may be widely or even globally distributed.

Figure 8:
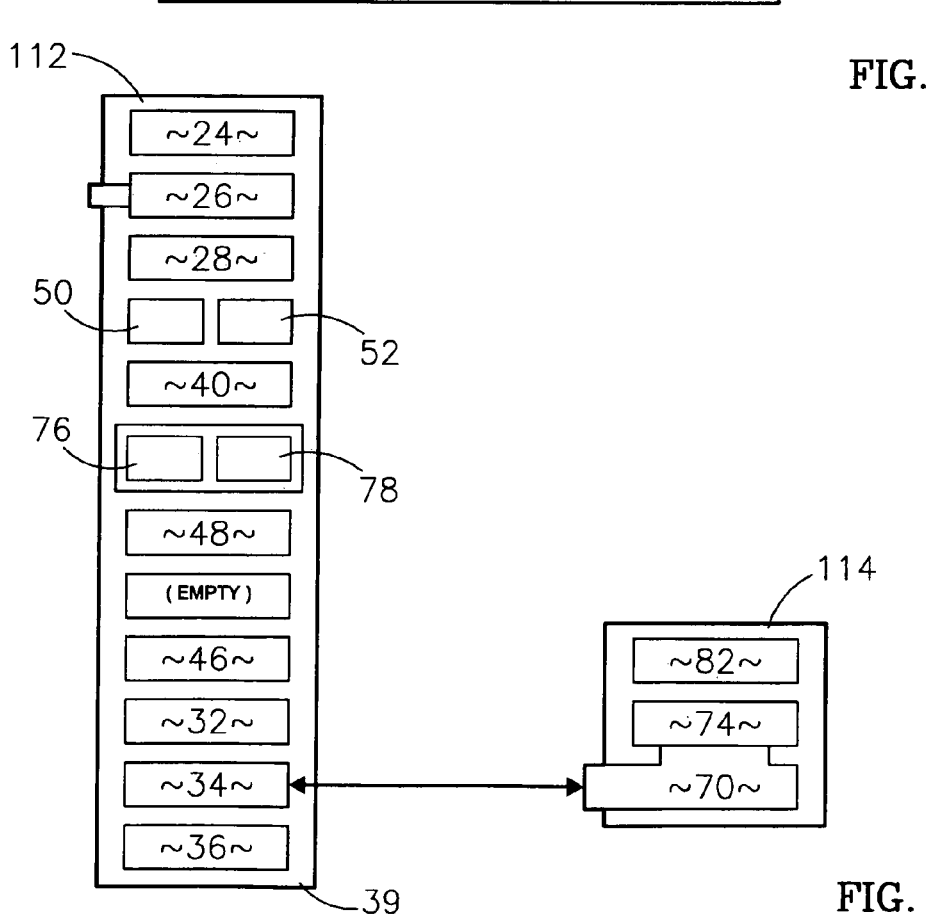
FIG. 8 is a block diagram showing elements in an alternative implementation of the IRAM unit 112 and OATS unit 114 of the system 10 of FIG. 1.

Although the invention has been described with reference to the preferred embodiments illustrated in the drawings, it is noted that equivalents may be employed and substitutions made herein without departing from the scope of the invention as recited in the claims. For example, referring to an alternate implementation shown in FIG. 8, the image analysis and recognition process may take place onboard the IRAM unit 112. In the implementation, the IRAM unit 112 includes or has access to the image analysis and recognition software 78 and library 76 of reference images previously described as being stored on or accessed by the OATS unit 14. The IRAM unit 112 identifies or attempts to identify the substance and transmits its results, along with the image and any other data, to the OATS unit 114, possibly in the form of a finished or preliminary report. Thereafter, this alternate implementation may function substantially similar to the implementation described above, with the OATS unit 114 uploading the report to the one or more data processing and storage servers 18 for subsequent access via the wide area network 16.

The invention claimed is:

1. A system for identifying and reporting a presence of a substance, the system comprising:
    a deployable data collection mechanism for collecting data for identifying the substance;
    a position-determining mechanism adapted to determine an actual geographic location of the deployable data collection mechanism;
    a database that associates a plurality of geographic locations with respective local reporting authorities and respective local reporting policies, such that the actual geographic location of the deployable data collection mechanism can be used to identify an appropriate local reporting authority and appropriate local reporting policy; and
    a transmitter adapted to transmit the actual geographic location and the data collected by the deployable data collection mechanism, and to contact the appropriate local reporting authority in accordance with the appropriate local reporting policy.

2. The system as set forth in claim 1, wherein the position-determining mechanism includes a global positioning system receiver.

3. A system for identifying and reporting a presence of a substance, the system comprising:
    a remote sensing unit including
        a position-determining location determination mechanism adapted to determine an actual geographic location of the remote sensing unit,
        a data collection mechanism for collecting data for identifying the substance, a first transmitter adapted to transmit the actual geographic location and the data collected by the data collection mechanism; and a control unit including a receiver adapted to receive the actual geographic location and the data transmitted by the remote sensing unit, a database that associates a plurality of geographic locations with respective local reporting authorities and respective local reporting policies, such that the actual geographic location of the remote sensing unit can be used to identify an appropriate local reporting authority and an appropriate local reporting policy, and a second transmitter adapted to transmit the actual geographic location and the data, and to notify the appropriate local reporting authorities in accordance with the appropriate local reporting policies.

4. The system as set forth in claim 3, wherein the position-determining mechanism includes a global positioning system receiver.

5. The system as set forth in claim 3, further including one or more remote data processing and storage servers for receiving the actual geographic location and the data transmitted by the control unit and making the data available to authorized persons, including the appropriate local reporting authority, via a wide area network.

6. A system for identifying and reporting a presence of a substance, the system comprising:

a remote sensing unit including a position-determining location determination mechanism adapted to determine an actual geographic location of the remote sensing unit, a data collection mechanism for collecting data for identifying the substance, a transmitter adapted to transmit the actual geographic location and the data collected by the data collection mechanism;

a control unit including a receiver adapted to receive the actual geographic location and the data transmitted by the remote sensing unit, a database that associates a plurality of geographic locations with respective local reporting authorities and respective local reporting policies, such that the actual geographic location of the remote sensing unit can be used to identify an appropriate local reporting authority and an appropriate local reporting policy, and a second transmitter adapted to transmit the actual geographic location and the data, and to notify the appropriate local reporting authorities in accordance with the appropriate local reporting policies; and one or more remote data processing and storage servers adapted to receive the actual geographic and the data transmitted by the control unit and to make the data available to authorized persons, including the appropriate local reporting authority, via a wide area network.

7. The system as set forth in claim 6, wherein the position-determining mechanism includes a global positioning system receiver.

* * * * *